(12) United States Patent
Stad et al.

(10) Patent No.: US 11,638,592 B2
(45) Date of Patent: May 2, 2023

(54) DISC NUCLEUS REMOVAL DEVICES AND METHODS

(71) Applicant: DePuy Synthes Products, Inc., Raynham, MA (US)

(72) Inventors: Shawn D. Stad, Raynham, MA (US); John Riley Hawkins, Cumberland, RI (US); Michael J. O'Neil, West Barnstable, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 1271 days.

(21) Appl. No.: 15/999,633

(22) Filed: Aug. 20, 2018

(65) Prior Publication Data

US 2019/0008549 A1    Jan. 10, 2019

Related U.S. Application Data

(60) Continuation of application No. 14/872,679, filed on Oct. 1, 2015, now Pat. No. 10,052,123, which is a
(Continued)

(51) Int. Cl.
*A61B 17/3207* (2006.01)
*A61B 17/00* (2006.01)

(52) U.S. Cl.
CPC ............. *A61B 17/320725* (2013.01); *A61B 2017/003* (2013.01); *A61B 2017/00261* (2013.01); *A61B 2017/00323* (2013.01)

(58) Field of Classification Search
CPC .. A61B 17/320725; A61B 2017/00261; A61B 2017/003; A61B 2017/00323
See application file for complete search history.

(56) References Cited

U.S. PATENT DOCUMENTS

| 3,320,957 A | 5/1967 | Sokolik |
| 3,924,608 A | 12/1975 | Mitsui |

(Continued)

FOREIGN PATENT DOCUMENTS

| JP | 53-105586 U | 8/1978 |
| JP | 60-135039 A | 7/1985 |

(Continued)

OTHER PUBLICATIONS

European Search Report of EP 07 77 7238 dated Feb. 2, 2012.
(Continued)

*Primary Examiner* — Ryan J. Severson
(74) *Attorney, Agent, or Firm* — Barnes & Thornburg, LLP

(57) ABSTRACT

Disclosed herein are devices and methods for removing tissue. In one aspect, a device for removing tissue includes a hollow elongate member having an outer wall and a lumen, a selectively deployable tissue-cutting element extending from the hollow elongate member, and an actuation member extending through the lumen and coupled to the hollow elongate member at a location that is distal to the tissue-cutting element. Movement of the actuation member can cause the tissue-cutting element to move from the insertion configuration where the tissue-cutting element is not deployed to a tissue-cutting configuration where the tissue-cutting element is deployed such that it is radially extended relative to the insertion configuration.

20 Claims, 8 Drawing Sheets

Related U.S. Application Data continuation of application No. 13/360,178, filed on Jan. 27, 2012, now Pat. No. 9,173,673, which is a division of application No. 11/427,848, filed on Jun. 30, 2006, now Pat. No. 8,109,957.

(56) References Cited

U.S. PATENT DOCUMENTS

| | | | |
|---|---|---|---|
| 4,646,722 A | 3/1987 | Silverstein et al. | |
| 4,697,576 A | 10/1987 | Krauter | |
| 5,025,778 A | 6/1991 | Silverstein et al. | |
| 5,030,201 A | 7/1991 | Palestrant | |
| 5,201,908 A | 4/1993 | Jones | |
| 5,217,001 A | 6/1993 | Nakao et al. | |
| 5,318,576 A | 6/1994 | Plassche, Jr. et al. | |
| 5,353,783 A | 10/1994 | Nakao et al. | |
| 5,386,817 A | 2/1995 | Jones | |
| 5,400,770 A | 3/1995 | Nakao et al. | |
| 5,431,322 A | 7/1995 | Green et al. | |
| 5,433,721 A | 7/1995 | Hooven et al. | |
| 5,433,739 A * | 7/1995 | Sluijter | A61B 18/1482 607/113 |
| 5,518,163 A | 5/1996 | Hooven | |
| 5,518,164 A | 5/1996 | Hooven | |
| 5,643,175 A | 7/1997 | Adair | |
| 5,810,807 A | 9/1998 | Ganz et al. | |
| 5,857,996 A * | 1/1999 | Snoke | A61B 1/3135 604/512 |
| 5,944,654 A | 8/1999 | Crawford | |
| 6,109,500 A | 8/2000 | Alli et al. | |
| 6,174,318 B1 | 1/2001 | Bates et al. | |
| 6,296,639 B1 | 10/2001 | Truckai et al. | |
| 6,458,076 B1 | 10/2002 | Pruitt | |
| 6,527,753 B2 | 3/2003 | Sekine et al. | |
| 6,596,005 B1 | 7/2003 | Kanz et al. | |
| 6,699,180 B2 | 3/2004 | Kobayashi | |
| 6,808,491 B2 | 10/2004 | Kortenbach et al. | |
| 6,824,509 B2 | 11/2004 | Yamaya et al. | |
| 7,740,633 B2 | 6/2010 | Assell et al. | |
| 8,109,957 B2 | 2/2012 | Stad et al. | |
| 8,348,950 B2 * | 1/2013 | Assell | A61B 17/32002 606/79 |
| 8,470,043 B2 * | 6/2013 | Schaller | A61B 17/3205 623/17.16 |
| 9,113,919 B2 * | 8/2015 | Assell | A61B 17/1664 |
| 9,161,773 B2 * | 10/2015 | Schaller | A61B 17/32056 |
| 9,173,673 B2 | 11/2015 | Stad et al. | |
| 10,052,123 B2 * | 8/2018 | Stad | A61B 17/320725 |
| 10,314,605 B2 * | 6/2019 | Huffmaster | A61B 17/320016 |
| 10,478,213 B2 * | 11/2019 | McPeak | A61B 17/320725 |
| 2002/0072745 A1 | 6/2002 | Truckai et al. | |
| 2002/0107530 A1 | 8/2002 | Sauer et al. | |
| 2002/0183591 A1 | 12/2002 | Matsuura et al. | |
| 2002/0183758 A1 | 12/2002 | Middleton et al. | |
| 2003/0036679 A1 | 2/2003 | Kortenbach et al. | |
| 2003/0130561 A1 | 7/2003 | Suzuki et al. | |
| 2003/0130564 A1 | 7/2003 | Martone et al. | |
| 2003/0176766 A1 | 9/2003 | Long et al. | |
| 2003/0176767 A1 | 9/2003 | Long et al. | |
| 2003/0176880 A1 | 9/2003 | Long et al. | |
| 2003/0208219 A1 | 11/2003 | Aznoian et al. | |
| 2004/0236424 A1 | 11/2004 | Berez et al. | |
| 2005/0049455 A1 | 3/2005 | Ootawara et al. | |
| 2005/0203527 A1 | 9/2005 | Carrison et al. | |
| 2005/0209610 A1 | 9/2005 | Carrison | |
| 2005/0261692 A1 * | 11/2005 | Garrison | A61B 17/1631 606/79 |
| 2006/0235271 A1 | 10/2006 | Carter et al. | |
| 2006/0247619 A1 | 11/2006 | Kaplan et al. | |
| 2008/0086157 A1 | 4/2008 | Stad et al. | |
| 2008/0132758 A1 | 6/2008 | Stefanchik et al. | |
| 2012/0179183 A1 | 7/2012 | Stad et al. | |
| 2016/0058466 A1 | 3/2016 | Stad et al. | |
| 2019/0008549 A1 * | 1/2019 | Stad | A61B 17/320725 |

FOREIGN PATENT DOCUMENTS

| | | |
|---|---|---|
| WO | 01/060262 A1 | 8/2001 |
| WO | 01/060270 A1 | 8/2001 |
| WO | 2004/049981 A2 | 6/2004 |

OTHER PUBLICATIONS

Japanese Office Action for Japanese Patent Application No. 2009-518126 dated Jan. 31, 2012.
Japanese Office Action dated Jul. 3, 2012 for Application No. 2009-518126 (6 Pages).
International Search Report and Written Opinion dated Sep. 4, 2008 for PCT/US07/12267.
International Preliminary Report Opinion dated Jan. 6, 2009 for PCT/US07/12267.

* cited by examiner

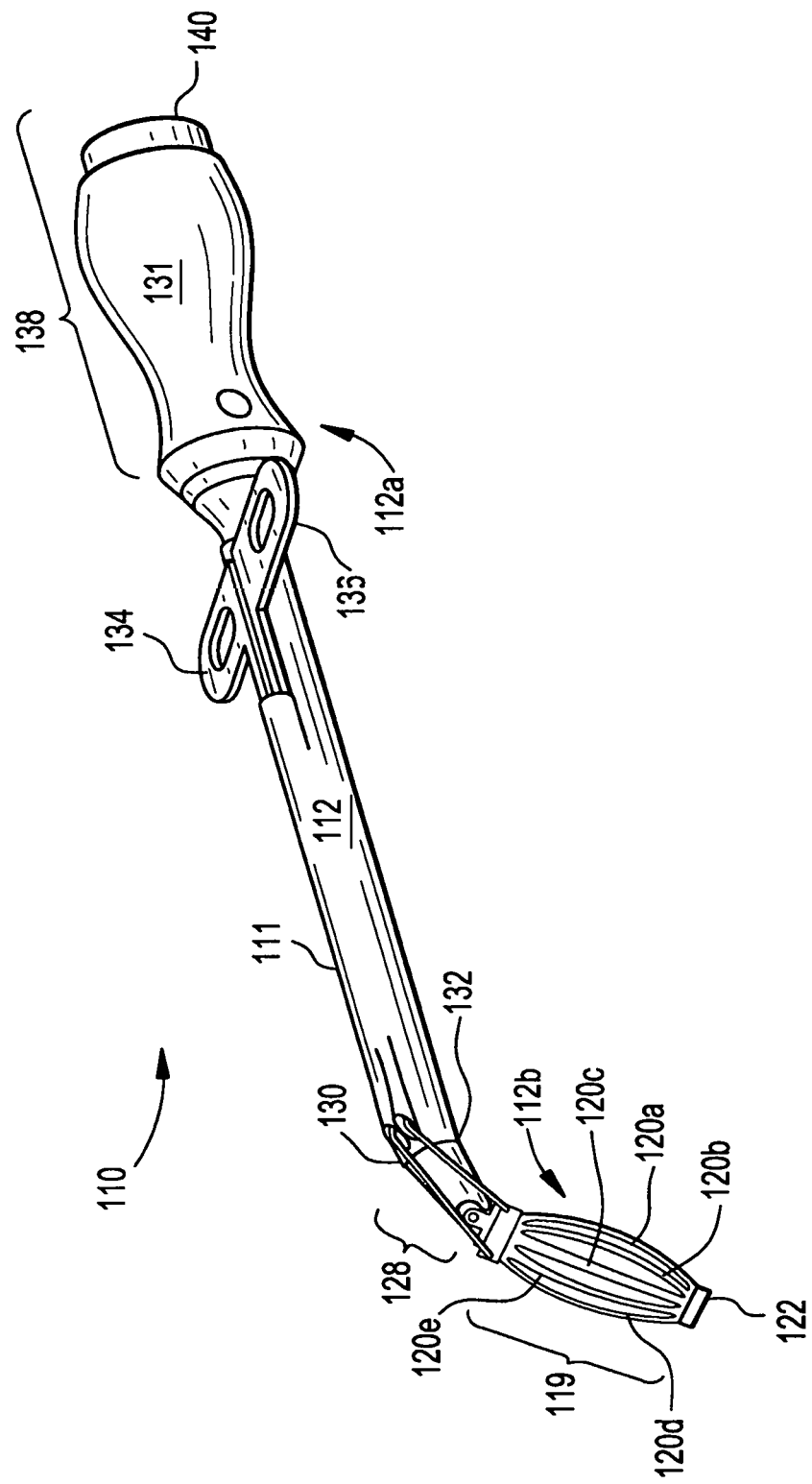

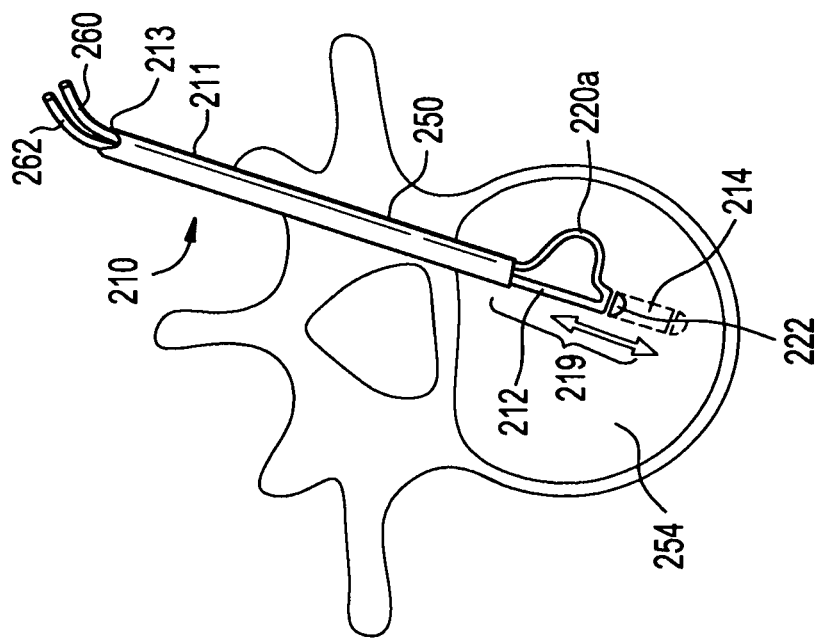
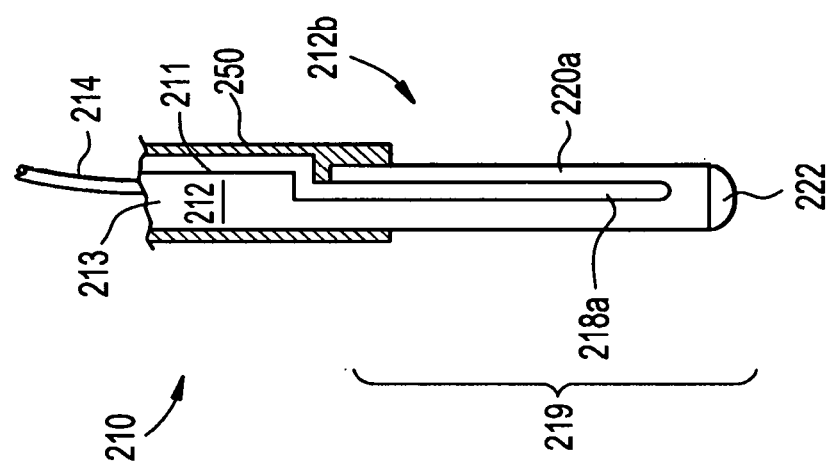

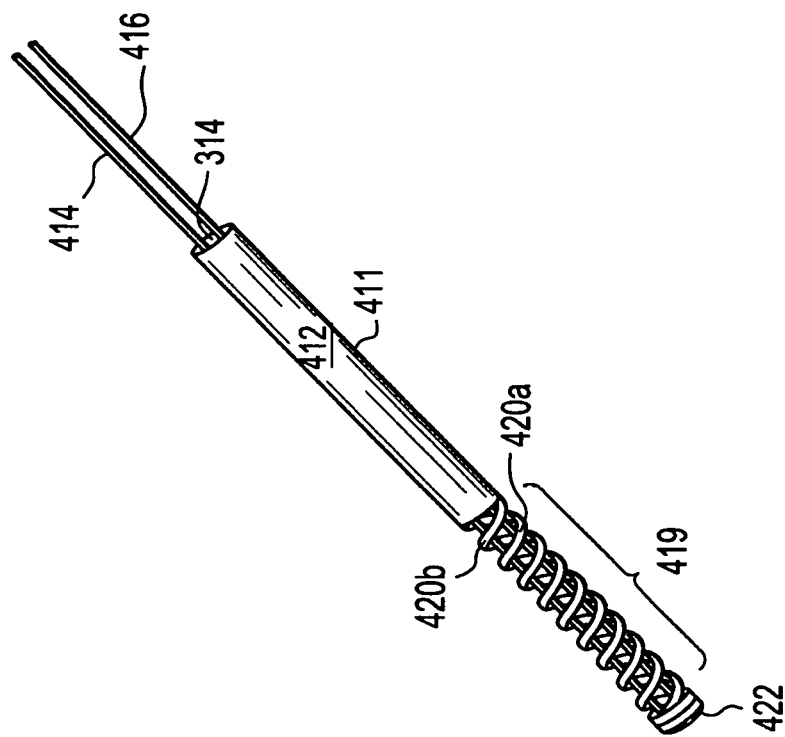
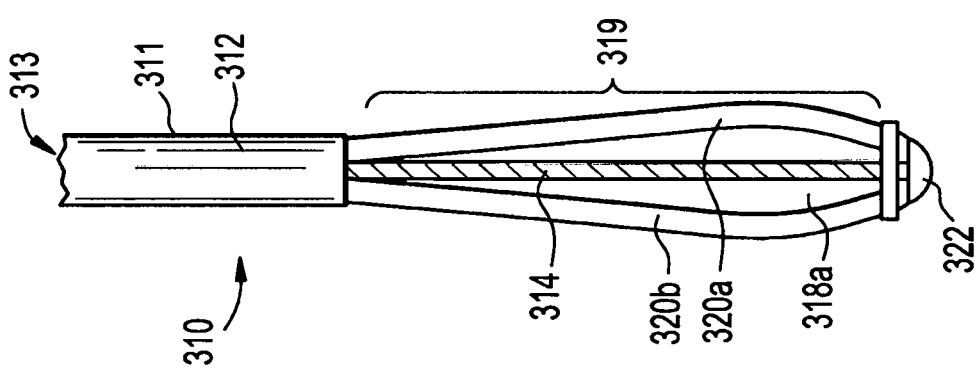

FIG. 6A
FIG. 6B
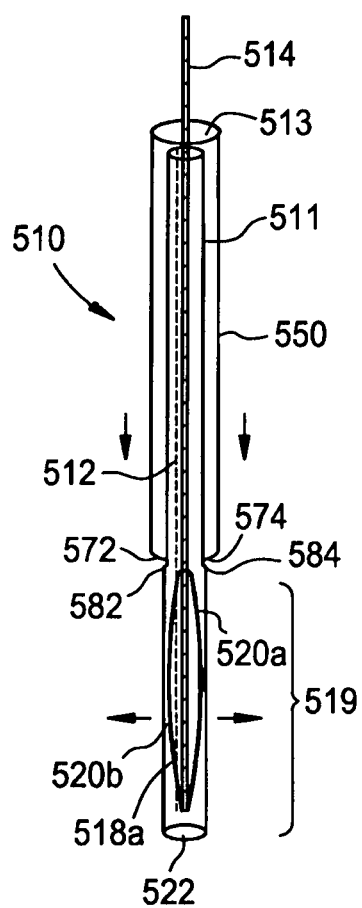
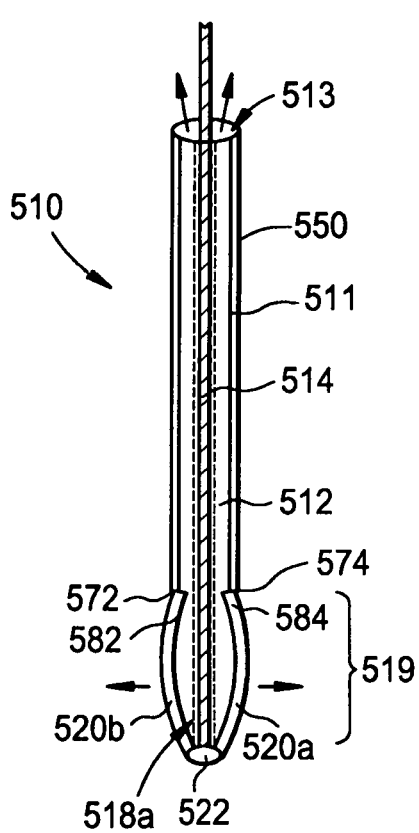

DISC NUCLEUS REMOVAL DEVICES AND METHODS

CROSS REFERENCE TO RELATED APPLICATIONS

This application is a continuation of U.S. patent application Ser. No. 14/872,679, filed on Oct. 1, 2015, and entitled "Disc Nucleus Removal Devices and Methods." U.S. patent application Ser. No. 14/872,679 is a continuation of U.S. application Ser. No. 13/360,178, filed on Jan. 27, 2012, entitled "Disc Nucleus Removal Devices And Methods," and now issued as U.S. Pat. No. 9,173,673. U.S. patent application Ser. No. 13/360,178 is a divisional of U.S. application Ser. No. 11/427,848, filed on Jun. 30, 2006, entitled "Disc Nucleus Removal Devices and Methods," and now issued as U.S. Pat. No. 8,109,957. Each of these applications is hereby incorporated by reference in its entirety.

FIELD OF THE INVENTION

The present invention relates to medical devices and methods for removing tissue, and in particular, to medical devices and methods for removing nucleus tissue from an intervertebral disc.

BACKGROUND OF THE INVENTION

The intervertebral discs that reside between each vertebra of the spine act as shock absorbers between the vertebrae. The disc itself consists of a tough outer layer called the annulus, and soft inner material, called the nucleus. The soft nucleus absorbs the majority of the shock as the body moves, keeping the spine supple and supported. As one ages, both the annulus and the nucleus lose some of their cushioning ability, and a greater portion of the pressure is borne by the outside of the disc, the annulus.

An artificial disc (also called a disc replacement, disc prosthesis or spine arthroplasty device) is a device that is implanted into the spine to imitate the functions of a normal disc (i.e., carry load and allow motion). There are many artificial disc designs classified into two general types: total disc replacement and disc nucleus replacement. As the names imply, with a total disc replacement, all or most of the disc tissue is removed and a replacement device is implanted into the space between the vertebra. With a disc nucleus replacement, only the center of the disc (the nucleus) is removed and replaced with an implant. The outer part of the disc (the annulus) is not removed. Disc nucleus replacement surgery offers certain benefits compared to total disc replacement. Since a disc nucleus replacement device is designed to replace only the nucleus of the disc, the procedure is less time consuming and possesses less risk to surrounding structures. Another benefit of disc nucleus replacement surgery is that it results in the retention of a greater amount of tissue, which gives the disc a greater regenerative capacity.

An important aspect of disc nucleus replacement surgery is to remove all of the nucleus material before installing the nucleus replacement device. In addition, care must be taken to avoid creating too large a defect in the annular wall. Incomplete or inadequate clearance of the disc nucleus, or formation of too large an annular defect, can cause the nucleus replacement to be expelled from or to extrude from the disc space.

Accordingly, there remains a need for improved devices and methods for removing nucleus tissue from an intervertebral disc, and in particular, devices and methods for removing nucleus tissue that minimize the required annular defect.

SUMMARY OF THE INVENTION

The present invention provides devices and methods for removing tissue. In one aspect, a device for removing tissue is provided that includes a hollow elongate member having an outer wall and a lumen, a selectively deployable tissue-cutting element extending from the hollow elongate member, and an actuation member extending through the lumen and communicating with the hollow elongate member at a location that is distal to the tissue-cutting element. Movement of the actuation member can cause the tissue-cutting element to move from the insertion configuration where the tissue-cutting element is not deployed to a tissue-cutting configuration where the tissue-cutting element is deployed such that it is radially extended relative to the insertion configuration. In use, the actuation member effects deployment of the tissue-cutting element by compression of the elongate member, and the compression is effected by rotation of a portion of the elongate member distal to the tissue-cutting element. In one embodiment, the actuation member and the elongate member are adapted to move independently of one another, and/or the tissue-cutting element is adapted to move independently of the elongate member.

The tissue-cutting element can have a variety of configurations. In one embodiment, the tissue-cutting element can be formed on at least a portion of the hollow elongate member. In another embodiment, the tissue-cutting element can be an arm that is formed by the portion of the elongate member that is between adjacent slits. The at least two adjacent slits can be formed in the outer wall of the elongate member and located proximal to a distal end of the elongate member. The slits can extend proximally over a distance that is less than a length of the elongate member. In other embodiments, the tissue-cutting element can include at least two radially-extendable arms that are formed between a plurality of slits. In alternate embodiments, the tissue-cutting element can be helically shaped and/or include a sharpened edge. The actuation member can also have a variety of configurations, however in one embodiment, the actuation member comprises at least one tether.

The device can also include a variety of other features to facilitate the removal of tissue. In one embodiment, the lumen of the elongate member can be adapted accommodate an irrigation fluid and/or suction. By way of non-limiting example, a fluid input conduit and a suction conduit can be disposed in the lumen. In another embodiment, the outer wall of the elongate member can be adapted to be positioned within a cannula. For example, the distal portion of the elongate member that includes the tissue-cutting element can include a ledge that abuts a shoulder of the cannula, such that the tissue-cutting element protrudes from the cannula.

The device can also include a locking mechanism that is adapted to hold the actuation member in the actuated position. Additionally or alternatively, the device can include a steering element that is adapted to control directional movement of the elongate member. The steering element can have a variety of configurations, and in one embodiment, the steering element is a joint formed between proximal and distal ends of the elongate member. In another embodiment, the steering element can be a tether that extends through the lumen of the elongate member and is coupled to the elongate member, which is flexible, at a location that is distal to the tissue-cutting element.

Methods for the removing tissue are also disclosed herein. In one aspect, a method for removing tissue includes positioning a tissue removal device at a site within a disc space, the tissue removal device having an elongate member with at least one selectively deployable tissue-cutting element and an actuation member. The method further includes applying a force to the actuation member to cause the tissue-cutting element to move from a non-deployed insertion configuration to a deployed, tissue-cutting configuration in which the tissue-cutting element is radially extended relative to the insertion configuration, and manipulating the tissue removal device within the disc space to cut and remove selected disc tissue. In one embodiment, the hollow elongate member is adapted move independently from the actuation member, and/or the tissue-cutting element is adapted to move independently of the elongate member.

The method can also include a variety of other steps to facilitate tissue removal. In one embodiment, the method can further include delivering fluid to the tissue site through the lumen. Alternatively or additionally, the method can include applying suction to the tissue site through the lumen and/or positioning at least a portion of the elongate member within a cannula for delivery to the disc space.

BRIEF DESCRIPTION OF THE DRAWINGS

The invention will be more fully understood from the following detailed description taken in conjunction with the accompanying drawings, in which:

FIG. 2 is a perspective view of another embodiment of a tissue removal device in a tissue-cutting configuration;

FIG. 3A is a perspective view of yet another embodiment of a tissue removal device in an insertion configuration;

FIG. 3B is a perspective view of the device of FIG. 3A positioned within a disc nucleus and in the tissue-cutting configuration;

FIG. 4 is a perspective view of another embodiment of a tissue removal device in a tissue-cutting configuration;

FIG. 5 is a perspective view of another embodiment of a tissue removal device in an insertion configuration;

FIG. 6A is a perspective view of another embodiment of a tissue removal device in an insertion configuration;

FIG. 6B is a perspective view of the device of FIG. 6A in the tissue-cutting configuration;

DETAILED DESCRIPTION OF THE INVENTION

Figure 1A:
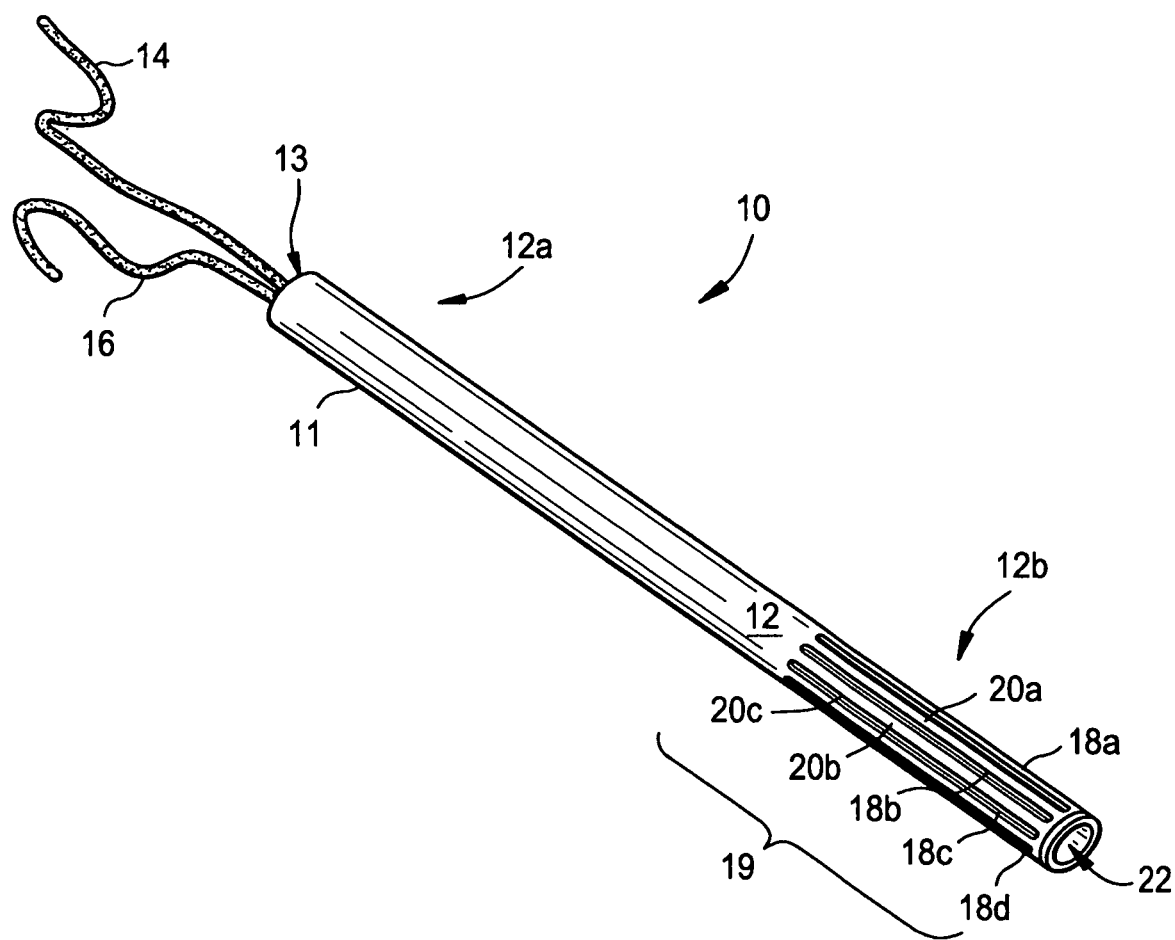
FIG. 1A is a perspective view of one embodiment of a tissue removal device disclosed herein in an insertion configuration.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides devices and methods for tissue removal. The tissue removal devices disclosed herein generally include an elongate member that has a tissue-cutting element formed on a distal end thereof. An actuation member can extend through the elongate member and couple to the tissue-cutting element to control or influence the configuration and/or orientation thereof. Upon actuation of the member, the sections of the elongate member that contain the tissue-cutting elements bow or deflect to expose cutting surfaces. The device can then be manipulated within a target site to cut tissue so that it can be removed by suction or other means. One skilled in the art will appreciate that the device can be used to remove a variety of types of tissue, however in an exemplary embodiment the device can be used in spinal surgery to remove disc nucleus tissue.

FIGS. 1A-1D illustrate one embodiment of a tissue removal device 10 that includes a hollow elongate member 12 having an outer wall 11 and a lumen 13, and one or more selectively deployable tissue-cutting elements 19 formed on at least a portion of the hollow elongate member 12. The device 10 can also include an actuation member 14 that extends through the lumen 13 to selectively activate the cutting elements 19. In one embodiment, the actuation member 14 is coupled to the hollow elongate member 12 at a location that is distal to the tissue-cutting element 19.

Figure 7:
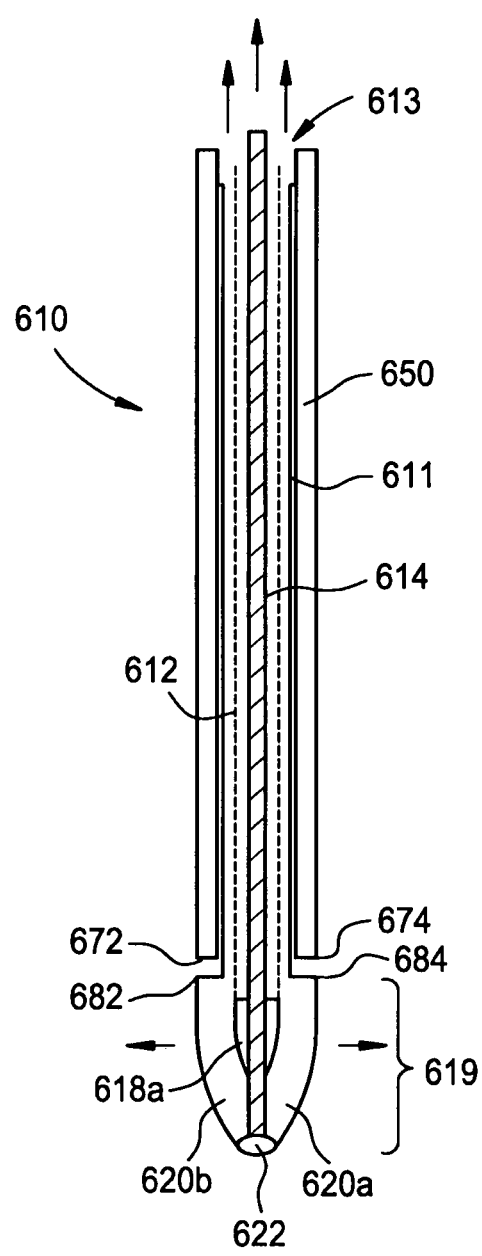
FIG. 7 is a perspective view of another embodiment of a tissue removal device in an insertion configuration.
Figure 8:
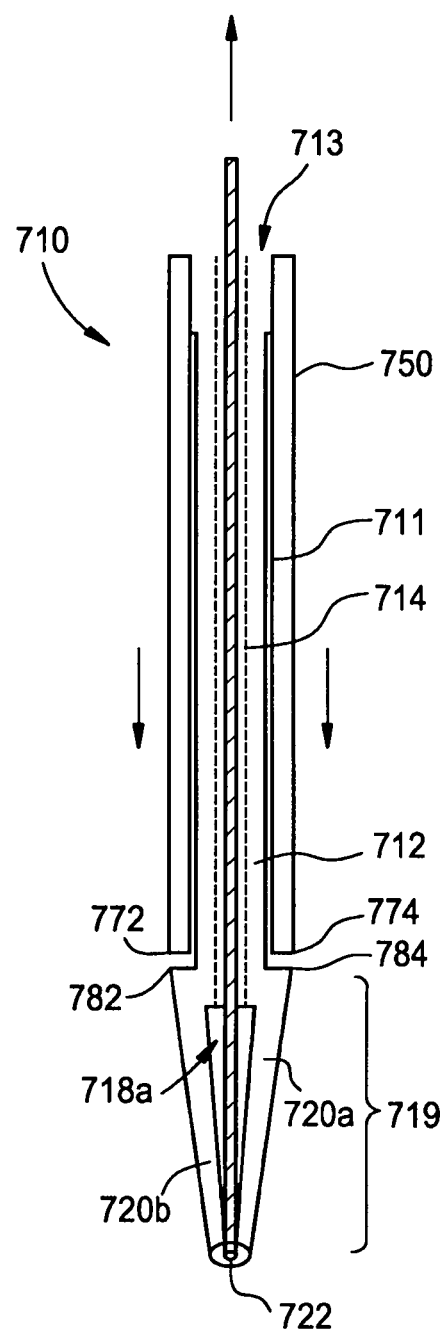
FIG. 8 is a perspective view of yet another embodiment of a tissue removal device in an insertion configuration.

The elongate member 12 can have virtually any configuration that allows it to be inserted to a surgical site. In one aspect, the member 12 is configured for delivery to the surgical site in a minimally invasive manner, such as via a cannula. As shown, the member 12 is substantially cylindrical and sufficiently strong to be inserted into tissue. The elongate member 12 can also include features to facilitate minimally invasive delivery, and as shown in FIGS. 7 and 8, which will be discussed in more detail below, the distal-most portion of the elongate member 612, 712 can be pointed or rounded. A lumen 13 can extend through at least a portion of the elongate member 12, and can be adapted to house an actuation member 14, discussed above. Further, the lumen 13 can accommodate an irrigation fluid and/or suction delivery to the tissue site, as will be discussed below. For example, as shown in FIGS. 3B and 5, which will also be discussed in more detail below, a fluid input conduit 260, 460 and a suction conduit 262, 462 can be disposed within the lumen 213, 413 to accommodate fluid delivery, and/or removal of tissue, such as by suction.

The elongate member 12 can have a variety of sizes, depending upon the intended use of the device 10. However, in one embodiment where the device 10 is used for disc nucleus removal, the elongate member 12 can have an outer diameter of about 5 mm (or less) when it is in the insertion configuration. The elongate member 12 can also be formed from a variety of materials, such as biocompatible metals, medical grade plastics, and/or combinations thereof. Exemplary biocompatible metals can include stainless steel, titanium, titanium alloys, cobalt chromium alloys, nitinol, and combinations thereof. Exemplary medical grade plastics can include nylon, polyolefins, ABS, PEEK, polysulfones, polyacetal, and combinations thereof.

Figure 1B:
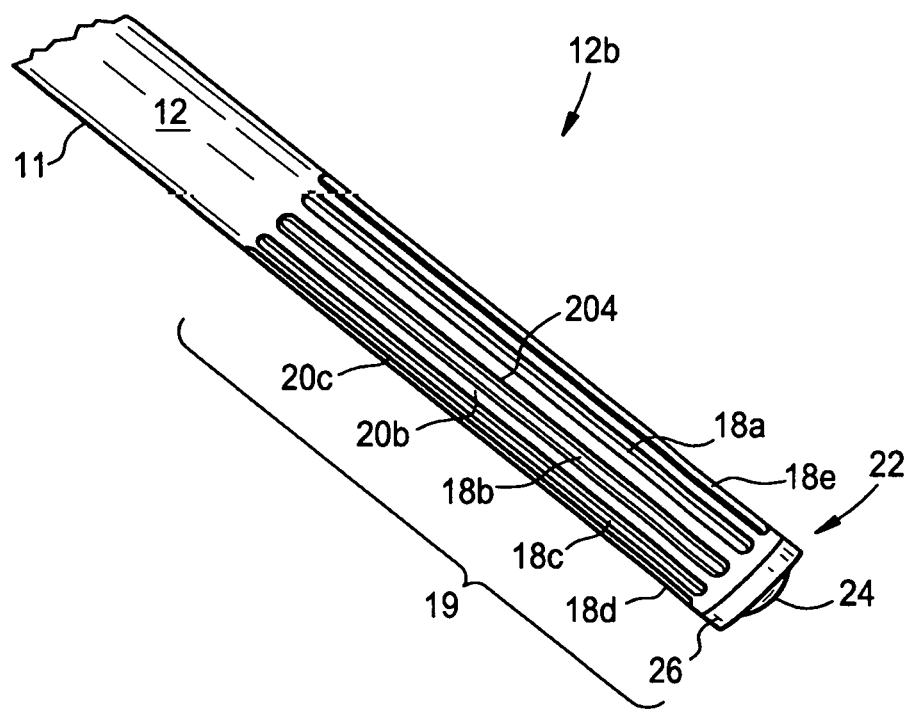
FIG. 1B is a perspective view of the distal end of the device of FIG. 1A in the insertion configuration.
Figure 1C:
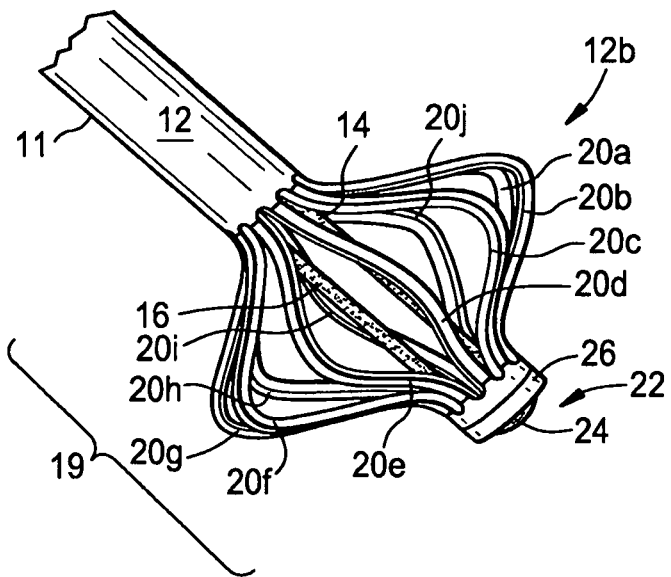
FIG. 1C is a perspective view of the distal end of the device of FIG. 1B in the tissue-cutting configuration.

At least one tissue-cutting element 19 can be formed on the distal end 12b of the member 12 that is able to be exposed (e.g., by extending radially) when subjected to a force. FIG. 1B illustrates the device 10 in which the tissue-cutting element 19 is in the insertion configuration where the tissue-cutting element 19 is not deployed to a tissue-cutting configuration, and FIG. 1C illustrates the device 10 where the tissue-cutting element 19 is deployed such that it is radially extended relative to the insertion configuration. The tissue-cutting element can be radially extended to a variety of diameters. For example, when the device is used to remove disc nucleus material, the device can have an outer diameter in the range of about 6 mm to 16 mm when in the tissue-cutting configuration.

The tissue-cutting element 19 can have any configuration that allows it to be configured to cut tissue (e.g., radially extend) upon the application of a force (e.g., compression) thereto. In one embodiment, the tissue-cutting element 19 can include at least one arm (arms 20a-20j are shown in FIGS. 1A-1D) that is formed as a result of adjacent slits (slits 18a-18e are shown in FIGS. 1A-1D) in the outer surface 11 of the elongate member 12. The slits can have a variety of shapes, and the shape of the slits can determine the shape of the resulting tissue-cutting arm. As shown in FIGS. 1A-1D, the slits 18a-18e can be substantially elongate, which can result in substantially elongate arms 20a-20j. In other embodiments, such as shown in FIG. 5, the slits can be formed in a spiral pattern which can result in substantially helical arms 420a, 420b. Alternatively, as shown in FIGS. 6A-8, the slits (slits 518a, 618a, 718a are shown) can be substantially ovular or triangular to form arms 520a-b, 620a-b, 720a-b having a complementary shape. The slits can also have a variety of sizes, depending upon the number of arms desired and the diameter of the elongate member, however when the device is used to remove nucleus disc material, the slits can have a width in the range of about 0.1 mm to 3 mm.

The arms can also have a variety of sizes depending upon the intended application of the device, however the arms can generally extend proximally from a position adjacent to the distal end of the device over a distance that is less than a length of the elongate member. By way of non-limiting example, when the device is used to remove disc nucleus material, the arms can be separated by a distance in the range of about 0.1 mm to 3 mm and extend a distance in the range of 5 mm to 50 mm along the elongate member. One skilled in the art will appreciate that a variety of techniques can be used to form the slits, and hence the arms, however in an exemplary embodiment, the slits can be formed by a laser cutting technique or an EDM technique.

While FIGS. 1A-1D illustrates a device that has about 10 arms 20a-20j that are radially disposed around the circumference of the elongate member 12, one skilled in the art will appreciate that the device can have any number of arms arranged in any configuration about the elongate member. The arms can also include a variety of features to facilitate cutting of tissue. For example, in one embodiment each arm can include at least one sharpened edge, at a leading edge of the device, that can act as a blade for cutting tissue. It is understood that the cutting elements need not include a sharpened edge, as the device can be configured for use with energy-assisting cutting such as, for example, by connection to a RF generator or an ultrasound transducer. One skilled in the art will appreciate that the shape and geometry of the cutting blades can be modified depending upon the type of cutting motion desired, that is forward, reverse, back and forth (i.e., wanding), side to side, or rotary cutting. For example, the angle of the cutting edge relative to the elongate member can vary whether a forward, reverse, back and forth (i.e., wanding), side to side, or rotary cut is desired.

A variety of techniques can be used to apply a force to the tissue-cutting elements to cause them to radially extend into a tissue-cutting configuration. In one embodiment, the device can include an actuation member that can extend through the elongate member and couple to the distal most portion of the tissue-cutting element. While the actuation member can have a variety of configurations, as shown in FIGS. 1A-1D, the actuation member can be two tethers 14, 16 or other cable-like element. A variety of techniques can be used to couple the actuation members to the tissue-cutting element. In one embodiment, as shown in FIGS. 1A-1D, the actuation members 14, 16 can be coupled to an end cap 22 that is positioned on the distal most end of the elongate member 12. The actuation members 14, 16 can be coupled to the center of the end cap 22 to prevent biasing of the device 10. While the end cap 22 can have a variety of configurations, as shown, it should be of a shape to facilitate ease of insertion. For example, it can be rounded or bullet-shaped. The end cap 22 can be formed of a single piece or it can be formed of a washer 26 and a nut 24. In use, a force, such as tension, can be applied to both of the actuation members 14, 16, which causes the end cap 22 to move towards the proximal end of the device 12a and compress the tissue-cutting element 19, thereby causing it to radially expand. The elongate member 12 can then be moved independently of the actuation members 14, 16 to cut tissue. Additionally, the tissue-cutting elements 20a-20j can also be moved independently of the elongate member 12 to cut tissue. While FIGS. 1A-1D illustrate a device 10 that has two actuation members 14, 16, in other embodiments such as FIG. 4, the device 310 can have one actuation member 314 that is disposed within the lumen 313 of the device 310 to effect actuation.

Figure 1D:
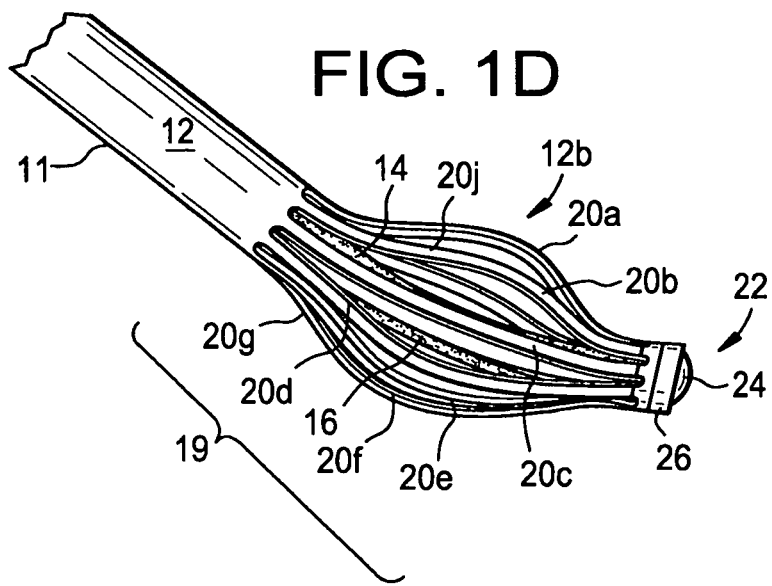
FIG. 1D is a perspective view of the distal end of the device of FIG. 1C following activation of a steering mechanism.

Referring back to FIGS. 1A-1D, the device 10 can also include a steering mechanism to facilitate directional motion. While the steering mechanism can have a variety of configurations, as shown the steering mechanism can be one of the tethers 14, 16 that extend through the elongate member 12 and are coupled to the distal end 12b or end cap 22 of the device 10. In other embodiments, the tether can be extend through the lumen of the device and be eccentrically coupled to the end cap to bias the device in one direction. In use, tension can be applied to one of the tethers 14,16 to cause the distal end 12b of the elongate member 12 to bend towards the direction of the tether being activated 14, 16, as shown in FIG. 1D.

FIG. 2 illustrates another embodiment of a tissue removal device 110. The device 110 is similar to the device 10 of FIGS. 1A-1D, and includes a hollow elongate member 112 having an outer wall 111 and a lumen (not shown) extending therethrough, a selectively deployable tissue-cutting element 119 formed on at least a portion of the hollow elongate member 112, and an actuation member (not shown) extending through the lumen and coupled to an end cap 122 located distal to the tissue-cutting element 119. The device 110 also includes a steering mechanism 128 to facilitate directional movement of the tissue-cutting element 119, and a handle 138. However, unlike the steering mechanism 19 described above with respect to FIGS. 1A-1D, which relies on bending the member 12 using tethers 14,16, the steering mechanism 128 includes a joint. As shown, the joint 128 is formed on the elongate member 112, at a position that is proximal to the tissue-cutting element 119. A variety of joints can be used, such as the U-joint 128 shown in FIG. 2. In use, tension can be applied to the joint 128 to bias the tissue-cutting element 119 to one side.

A variety of techniques can be used to facilitate motion of the joint 128. By way of non-limiting example, two pull wires 130, 132 can extend through at least a portion of the elongate member 112 and couple to elongate member 112 at a location that is distal to the joint 128. Control elements 134, 136 can be formed on the proximal end of the wires 130, 132 and can be used to grip and apply tension to one of the wires 130, 132 to effect directional movement of the tissue-cutting element 119. While FIG. 2 shows control elements 134, 136 formed on the wires 130, 132, in other embodiments, the wires can extend through a handle formed on the proximal end of the elongate member, and can be coupled to a lever, knob, or dial that can be activated to cause tension to be applied thereto.

As noted above, the elongate member 112 can also include a handle 138 that is located on the proximal end 112a thereof to facilitate manipulation and handling of the device 110. While the handle 138 can have any configuration that allows a user to conveniently hold and operate the device 110, in one embodiment the handle 138 has a substantially elongate shape. The handle 138 can include features to facilitate actuation of the actuation member. For example, the handle 138 can include a sliding actuator lever 131 that can be coupled to the actuation member and that allows tension to be selectively applied thereto. In alternate embodiments, rotatable knobs or dials can be used to selectively apply tension to the actuation member. A locking mechanism (not shown) can also be associated with the sliding actuator lever to hold the actuation member in a desired position once tension is applied.

The handle 138 can also include a driving mechanism to facilitate movement of the tissue-cutting element 119 to effect cutting of tissue when it is in the tissue-cutting configuration. For example, as shown, the handle 138 can include a rotatable knob 140 to effect rotational movement of the tissue-cutting element 119. Additionally, the handle can include features to facilitate the removal of tissue, such as a port for delivering suction and/or irrigation to the elongate member, or it can be adapted to couple to an external suction and/or irritation port. One skilled in the art will appreciate the variety of features that can be formed on the handle.

FIGS. 3A-8 illustrate other embodiments of a tissue removal device 210, 310, 410, 510, 610, 710. The device 210 of FIGS. 3A-3B is similar to the device 10 of FIGS. 1A-1D, and includes a hollow elongate member 212 having an outer wall 211 and a lumen 213, and a selectively deployable tissue-cutting element 219 formed on at least a portion of the hollow elongate member 212. The device 210 also includes an actuation member 214 that extends through the lumen 213 and is coupled to an end cap 222 located distal to the tissue-cutting element 219. However, the device 210 shown in FIGS. 3A-3B, unlike the device 10 of FIGS. 1A-1D, has a single cutting arm 220a that is formed as a result of the formation of two slits (slit 118a is shown) in the elongate member 212. Such a single cutting arm 220a can be used for directional cutting. As shown in FIG. 3B, when a force (e.g., tension or a rotational force applied to threaded members) is applied to move the device 210 from the insertion configuration to the tissue-cutting configuration, the tissue-cutting element 119 is radially extended in only one direction, and used to cut tissue in a certain area, for example by a back and forth motion or a rotary motion. Once cut, the tissue can be removed from the tissue site by the application of fluid and/or suction through fluid input conduit 260 and/or suction conduit 262 that are disposed within the lumen 213, as noted above.

FIG. 4 illustrates another embodiment of a tissue removal device 310. The device 310 is also similar to the device 10 of FIGS. 1A-1D, and includes a hollow elongate member 312 having an outer wall 311 and a lumen 313, and a selectively deployable tissue-cutting element 319 formed on at least a portion of the hollow elongate member 312. The device 310 also includes an actuation member 314 that extends through the lumen 313 and is coupled to an end cap 322 located distal to the tissue-cutting element 319. However, unlike the device 10 in FIGS. 1A-1D, the device 310 can have two opposed tissue-cutting elements 320a, 320b that are formed as a result of two slits (slit 318a is shown). The device 310 can also have an actuation member 314 that is threadably mated to end cap 322. As the actuation member is rotated, a compressive force will be applied to end cap 322, causing the arms 320a, 320b to bow out. This results in the device 310 having a bulb-shaped configuration when in the tissue-cutting configuration. Although the actuation of the embodiment shown in FIG. 4 is described with respect to rotation of a threaded member, one skilled in the art will understand that tension can alternatively be applied to the actuation member.

FIG. 5 illustrates yet another embodiment of a tissue removal device 410. The device 410 is similar to the device 10 of FIGS. 1A-1D, and includes a hollow elongate member 412 having an outer wall 411 and a lumen 413, and a selectively deployable tissue-cutting element 419 formed on at least a portion of the hollow elongate member 412. The device 410 also includes an actuation member 414 that extends through the lumen 413 and is coupled to an end cap 422 located distal to the tissue-cutting element 419. However, unlike the device 10 in FIGS. 1A-1D, the device 410 includes helically shaped cutting elements 420a, 420b that are formed as result of spirally cut slits. The cutting member can be formed as a result of a single helix, or numerous helices formed in or extend from the elongate member. In use, force (e.g., tension or a rotational force applied to threaded members) is applied to compress the outer walls of the helix, thereby causing expansion thereof. When in the tissue-cutting configuration, the device 410 can be substantially tubular in shape, having a substantially constant diameter. Additionally, and when moved to cut tissue (e.g., by rotation of the helical cutting elements 420, 420b), the helically-shaped cutting elements 420a, 420b can help initiate tissue movement into the device 410.

FIGS. 6A-6B illustrate yet another embodiment of a tissue removal device 510. The device 510 is similar to the device 10 of FIGS. 1A-1D, and includes a hollow elongate member 512 having an outer wall 511 and a lumen 513, and a selectively deployable tissue-cutting element 519 formed on at least a portion of the hollow elongate member 512. The device 510 also includes an actuation member 514 that extends through the lumen 513 and is coupled to an end cap 522 located distal to the tissue-cutting element 519. However, unlike the device 10 in FIGS. 1A-1D, the device 510 includes two substantially ovular slits (slit 518a is shown) that form arms 520a, 520b. In use, a force is applied to compress the arms 520a, 520b and the device 510 moves from the insertion configuration (FIG. 6A) to the tissue-cutting configuration (FIG. 6B), and the arms 520a, 520b extend radially to cut tissue.

The device 510 can also include features that facilitate insertion within a cannula 550. While a variety of features can be used, as shown each elongate member 512 can include opposed ledges 582, 584 that are formed thereon at a location that is proximal to the tissue-cutting element 519. The ledges 582, 584 are adapted to abut corresponding shoulders 572, 574 that are formed on a cannula 550. One skilled in the art will appreciate that the ledges and shoulders can have a variety of sizes, depending upon the intended use of the device. In use, and as a force (i.e., tension) is applied to the actuation member 514, the ledge 582, 584 is pressed against the shoulder 572, 574 to facilitate the radial expansion of the tissue-cutting element 519.

FIG. 7 illustrates yet another embodiment of a tissue removal device 610. The device 610 is similar to the device 10 of FIGS. 1A-1D, and includes a hollow elongate member 612 having an outer wall 611 and a lumen 613, and a selectively deployable tissue-cutting element 619 formed on at least a portion of the hollow elongate member 612. The device 610 also includes an actuation member 614 that extends through the lumen 613 and is coupled to an end cap 622 located distal to the tissue-cutting element 619. However, unlike the device 10 in FIGS. 1A-1D, the device 610 includes two substantially triangular slits (slit 618a is shown) that form arms 620a, 620b. The device 610 can also include features that facilitate insertion within a cannula 650. As noted above, the elongate member 612 of the device 610 can include a substantially rounded distal end. Additionally, and similar to the device 510 of FIGS. 6A-6B, each elongate member 612 can include opposed ledges 682, 684 that are formed thereon at a location that is proximal to the tissue-cutting element 619. The ledges 682, 684 are adapted to abut corresponding shoulders 672, 674 that are formed on a cannula 650. In use, and as a force (e.g., tension) is applied to the actuation member 614, the ledge 682, 684 is pressed against the shoulder 672, 674 to facilitate the radial expansion of the tissue-cutting element 619.

FIG. 8 illustrates yet another embodiment of a tissue removal device 710. The device 710 is similar to the device 10 of FIGS. 1A-1D, and includes a hollow elongate member 712 having an outer wall 711 and a lumen 713, and a selectively deployable tissue-cutting element 719 formed on at least a portion of the hollow elongate member 712. The device 710 also includes an actuation member 714 that extends through the lumen 713 and is coupled to an end cap 722 located distal to the tissue-cutting element 719. However, unlike the device 10 in FIGS. 1A-1D, the device 710 includes two substantially triangular slits (slit 718a is shown) that form arms 720a, 720b. The device 710 can also include features that facilitate insertion within a cannula 750. As noted above, the elongate member 712 of the device 710 can include a substantially pointed distal end. Additionally, and similar to the device 510 of FIGS. 6A-6B, each elongate member 712 can include opposed ledges 782, 784 that are formed thereon at a location that is proximal to the tissue-cutting element 719. The ledges 782, 784 are adapted to abut corresponding shoulders 772, 774 that are formed on a cannula 750. In use, and as a force (i.e., tension) is applied to the actuation member 714, the ledge 782, 784 is pressed against the shoulder 772, 774 to facilitate the radial expansion of the tissue-cutting element 719.

One skilled in the art will appreciate that each of the various designs provides for disc removal with cutting surfaces. The cutting surfaces can be located along the leading edge(s) of the blade(s) and can be tapered to a relatively sharp cutting tip or plane. The helically shaped cutting elements allow for cutting via rotary motions prompting the collection of the loose disc tissue in the central portion of the device and for aspiration with the central cannula. The multiple blades of the helical shaped cutting element provide for the exposure of additional cutting surfaces for each rotation when compared to the dual blade device shown in FIG. 4. This added exposure reduces the number of rotations required to remove tissue. In addition, the multi-blade helical device allows for one blade to pull/tension the tissue and the second to cut under tension, this can also enhance the ability to remove tissue.

The devices disclosed herein can be used to remove tissue from, for example, the nucleus of a disk. While the method is described in connection with device of FIGS. 3A-3B, a person skilled in the art will appreciate that various other devices can be used. In one embodiment, and following preparation of the patient and surgical site as is known in the art, the device can be inserted to the target tissue, e.g., the nucleus of the disc, via a hole in the annular wall. As shown in FIG. 3B, the device 210 can be inserted through a cannula 250 to position the device 210 within the disc nucleus 254. The device 210 is preferably inserted in the insertion configuration, as shown in FIG. 3A. Such an insertion configuration is particularly advantageous in that it minimizes the size of the annular defect and enables the use of minimally invasive surgical techniques. Once inserted into the disc nucleus material, and if the device includes a steering mechanism, the steering mechanism can be activated to further position the device within the disc at the site of the tissue to be removed.

Once the device 210 is positioned within the nucleus 254, a force can be applied to the actuation member 214. For embodiments where the actuation member is a tether 214, the tether 214 can be pulled in the proximal direction to cause the tissue-cutting element to radially expand to the tissue-cutting configuration. Depending upon the configuration of the device, the tension can be applied to the tether directly, or by movement of a lever, dial, or knob formed on a handle of the device. As a result, the device 210 moves from the insertion configuration to the tissue-cutting configuration, where the tissue-cutting arm 220a is radially expanded relative to the elongate member 212, as shown in FIG. 3B. The actuation member can then optionally be locked in position using a locking mechanism to maintain the radial expansion of the tissue-cutting element.

Once the device is in the tissue-cutting configuration, the device can be moved to cut tissue, and it can be steered, as appropriate, to reach areas of the nucleus that require removal of tissue. Depending upon the type of tissue cut desired, the device can be rotated, moved forward, or moved in reverse. One skilled in the art will appreciate that movement of the device can be effected by directly moving the elongate member, by moving a lever, dial, or knob on the handle of the device, and/or by activating an energy source to deliver energy to the tissue-cutting element. As the tissue is being cut, or alternatively, once all of the tissue is cut, the tissue fragments can be removed from the disc. While a variety of removal techniques can be used, in one embodiment and still referring to FIG. 3B, suction and/or irrigation can be applied through a fluid input conduit 260 and a suction conduit 262 that are disposed within the lumen 213. In other embodiments, the elongate member can be removed and a separate tissue removal device can be inserted into the nucleus space to clear the tissue.

Following the removal of the tissue, the locking mechanism can optionally be unlocked and the force that is applied to the actuation member released. This causes the tissue-cutting element to radially retract back to the insertion configuration. The device can then be removed from the tissue, leaving behind a substantially tissue-free nucleus space and minimizing the size of the annular defect.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A method for removing tissue, comprising:
    positioning a tissue removal device at a site within a disc space, the tissue removal device having an elongate member defining a distal end comprising at least one selectively deployable tissue-cutting element, an actuation member configured to actuate the at least one tissue-cutting element, and a steering mechanism connecting the tissue-cutting element to a distal end of the elongate member;
    applying a force to the steering mechanism to steer the tissue-cutting element;
    applying a force to the actuation member to cause a distal end cap of the at least one selectively deployable tissue-cutting element to move in a linear proximal direction such that the tissue-cutting element moves from a non-deployed insertion configuration to a deployed, tissue-cutting configuration;
    wherein, in the tissue-cutting configuration, the tissue-cutting element is radially extended relative to the insertion configuration; and
    manipulating the tissue removal device within the disc space to cut and remove selected disc tissue.

2. The method of claim 1, wherein applying the force to the steering mechanism to steer the tissue-cutting element further comprises biasing the tissue-cutting element to one side.

3. The method of claim 1, wherein the steering mechanism further comprises a joint and at least one pull wire coupled to the joint, and applying the force to the steering mechanism further comprises applying tension to the at least one pull wire to pivot the joint and effect directional movement of the tissue cutting element.

4. The method of claim 3, wherein the joint is adapted to move independently from the elongate member.

5. The method of claim 1, wherein the at least one tissue-cutting element is adapted to move independently from the elongate member.

6. The method of claim 1, further comprising delivering fluid to the disc space through a lumen formed in the elongate member.

7. The method of claim 1, further comprising applying suction to the disc space through a lumen formed in the elongate member.

8. The method of claim 1, further comprising positioning at least a portion of the elongate member within a cannula for delivery to the disc space.

9. The method of claim 1, further comprising actuating a locking mechanism of the tissue cutting device to hold the actuation member in a desired position.

10. The method of claim 1, further comprising actuating a driving mechanism of the tissue removal device to move the tissue-cutting element to cut tissue.

11. A method for removing tissue, comprising:
    positioning a tissue removal device at a site within a disc space, the tissue removal device having an elongate member defining a distal end comprising at least one selectively deployable tissue-cutting element, an actuation member configured to actuate the tissue-cutting element, and a U-joint connecting the tissue-cutting element to a distal end of the elongate member;
    pivoting the tissue-cutting element relative to the elongate member about the U-joint and at least one axis that is perpendicular to a central longitudinal axis of the elongate member;
    applying a force to the actuation member to cause a distal end cap of the at least one selectively deployable tissue-cutting element to move in a linear proximal direction such that the tissue-cutting element moves from a non-deployed insertion configuration to a deployed, tissue-cutting configuration; and
    manipulating the tissue removal device within the disc space to cut and remove selected disc tissue.

12. The method of claim 11, wherein the elongate member is adapted to move independently from the U-joint.

13. The method of claim 11, wherein the at least one selectively deployable tissue-cutting element is adapted to move independently from the elongate member.

14. The method of claim 11, further comprising delivering fluid to the disc space through a lumen formed in the elongate member.

15. The method of claim 11, further comprising applying suction to the disc space through a lumen formed in the elongate member.

16. The method of claim 11, further comprising positioning at least a portion of the elongate member within a cannula for delivery to the disc space.

17. The method of claim 11, further comprising actuating a locking mechanism of the tissue cutting device to hold the actuation member in a desired position.

18. The method of claim 11, further comprising actuating a driving mechanism of the tissue cutting device to move the tissue-cutting element to cut tissue.

19. The method of claim 11, wherein the tissue removal device further includes at least one pull wire extending from a proximal end of the elongate member to a distal end of the U-joint, and wherein pivoting the tissue-cutting element further comprises applying a force to the at least one pull wire to pivot the U-joint.

20. The method of claim 19, wherein the at least one wire includes a first pull wire and a second pull wire, wherein the first and second pull wires are attached to the U-joint at two different locations.

* * * * *